US012788635B2

(12) United States Patent
Arba Mosquera et al.

(10) Patent No.: US 12,788,635 B2
(45) Date of Patent: Nov. 10, 2026

(54) METHODS FOR CONTROLLING A LASER OF A PROCESSING APPARATUS AND PERFORMING A SURGICAL PROCEDURE FOR THE SEPARATION OF A VOLUME BODY, A PROCESSING APPARATUS, A COMPUTER PROGRAM AND A COMPUTER-READABLE MEDIUM

(71) Applicant: SCHWIND eye-tech-solutions GmbH, Kleinostheim (DE)

(72) Inventors: Samuel Arba Mosquera, Aschaffenburg (DE); Mario Shraiki, Ober-Ramstadt (DE)

(73) Assignee: SCHWIND eye-tech-solutions GmbH, Kleinostheim (DE)

(*) Notice: Subject to any disclaimer, the term of this patent is extended or adjusted under 35 U.S.C. 154(b) by 494 days.

(21) Appl. No.: 18/365,562

(22) Filed: Aug. 4, 2023

(65) Prior Publication Data

US 2024/0041655 A1 Feb. 8, 2024

(30) Foreign Application Priority Data

Aug. 8, 2022 (DE) ..................... 10 2022 119 922.3

(51) Int. Cl.
*A61F 9/008* (2006.01)

(52) U.S. Cl.
CPC *A61F 9/00827* (2013.01); *A61F 2009/00872* (2013.01)

(58) Field of Classification Search
None
See application file for complete search history.

(56) References Cited

U.S. PATENT DOCUMENTS

2007/0282313 A1 12/2007 Huang et al.
2017/0113304 A1 4/2017 Pluss et al.
(Continued)

FOREIGN PATENT DOCUMENTS

CN 101616647 A 12/2009
CN 114617708 A 6/2022
(Continued)

OTHER PUBLICATIONS

Office Action issued May 23, 2023 in DE Appl. No. 10 2022 119 922.3.
(Continued)

*Primary Examiner* — Michael T. Holtzclaw
(74) *Attorney, Agent, or Firm* — MEDLER FERRO WOODHOUSE & MILLS PLLC

(57) ABSTRACT

A method is disclosed for controlling a laser for the separation of a volume body with an anterior interface and with a posterior interface. The method includes determining a depth relief of the volume body to be generated between the anterior interface and the posterior interface, determining a reference point of an axis of symmetry of the determined depth relief or of a respective interface by means of the control device, and controlling the laser starting from the determined reference point in tracks circle-like at least in certain areas such that the laser emits pulsed laser pulses in a shot sequence in a predefined pattern into the material. The interfaces are generated by means of an interaction of the individual laser pulses with the cornea by the generation of a plurality of cavitation bubbles along the circle-like tracks. Further disclosed are a processing apparatus, computer program and computer-readable medium.

29 Claims, 2 Drawing Sheets

(56) References Cited

U.S. PATENT DOCUMENTS

| | | | | |
|---|---|---|---|---|
| 2021/0052423 | A1* | 2/2021 | Arba-Mosquera | A61F 9/00825 |
| 2021/0177651 | A1* | 6/2021 | Loerner | A61F 9/0084 |
| 2021/0346198 | A1* | 11/2021 | Arba Mosquera | A61F 9/00827 |
| 2022/0040001 | A1 | 2/2022 | Mosquera et al. | |

FOREIGN PATENT DOCUMENTS

| | | | | |
|---|---|---|---|---|
| DE | 102019135609 | A1 * | 6/2021 | A61F 9/00827 |
| DE | 10 2020 104 687 | A1 | 8/2021 | |
| DE | 10 2021 116 497 | A1 | 12/2022 | |
| JP | 2015198986 | A | 11/2015 | |
| JP | 2017086153 | A | 5/2017 | |
| WO | 2009059251 | A2 | 5/2009 | |

OTHER PUBLICATIONS

Office Action issued on Jun. 12, 2026 in corresponding CN Appln. No. 202310964331.3.

* cited by examiner

METHODS FOR CONTROLLING A LASER OF A PROCESSING APPARATUS AND PERFORMING A SURGICAL PROCEDURE FOR THE SEPARATION OF A VOLUME BODY, A PROCESSING APPARATUS, A COMPUTER PROGRAM AND A COMPUTER-READABLE MEDIUM

FIELD

The invention relates to a method for controlling a laser of a processing apparatus, as well as to a method for performing a surgical procedure for the separation of a volume body with an anterior interface and with a posterior interface from a material. Further, the invention relates to a processing apparatus, to a computer program as well as to a computer-readable medium.

BACKGROUND

Opacities and scars within the cornea, which arise by inflammations, injuries or native diseases, as well as visual disorder such as for example myopia or hyperopia, impair the sight. In particular in case that these pathological and/or unnaturally altered areas of the cornea are located in the axis of vision of the eye, a clear sight is considerably disturbed. In known manner, the thus altered areas are eliminated by a so-called phototherapeutic keratectomy (PTA) by means of an ablatively acting laser, for example an excimer laser. However, this is only possible if the pathological and/or unnaturally altered areas of the cornea are located in the superficial layers of the cornea. Areas located deeper, in particular within the stroma, are not reachable by means of ablative laser methods. Here, additional measures, such as for example the exposure of the areas located deeper by means of an additional corneal incision, have to be taken.

Therein, it is in particular known that in using so-called femtosecond systems, corresponding x-y-z movements are performed in the space to generate corresponding cavitation bubbles to generate an extractable lenticule, which allows the correction. Therein, the z-direction, in other words the depth direction, is in particular problematic since the entire laser device has to be moved therein. Thus, problems arise, for example in the speed or in the control of the laser device, in particular to move the laser device in the corresponding z-di recti on.

In order to be able to perform an advantageous treatment on the patient, it is in particular important that a correspondingly accurate generation of the cavitation bubbles as well as, to shorten the treatment time, the cavitation bubbles can be correspondingly fast generated.

Therefore, it is the object of the present invention to provide a method and a processing apparatus for controlling a laser for the separation of the volume from a human or animal cornea, as well as to a method for performing a surgical procedure, by which the disadvantages of the prior art are overcome. In particular, it is an object of the invention to be able to generate the volume body in technically simple manner.

SUMMARY

This object is solved by a method, a processing apparatus, a computer program as well as a computer-readable medium according to the independent claims. Advantageous configurations with convenient developments of the invention are specified in the respective dependent claims, wherein advantageous configurations of the method are to be regarded as advantageous configurations of the processing apparatus, of the computer program and of the computer-readable medium and vice versa.

Therein, a first aspect of the invention relates to a method for controlling a laser of a processing apparatus, as well as a method for performing a surgical procedure, for the separation of a volume body with an anterior interface and with a posterior interface from a material, in particular a cornea of an eye, in particular a human or animal cornea. Therein, the method is performed by means of a control device of the processing apparatus. Determining a depth relief of the volume body to be generated between the anterior interface and the posterior interface is effected depending on at least one information, in particular patient information. A reference point of an axis of symmetry of the determined depth relief or of a respective interface is determined by means of a control device of the processing apparatus. The laser is controlled in tracks circle-like at least in certain areas starting from the determined reference point such that it emits pulsed laser pulses in a shot sequence in a predefined pattern into the material, wherein the interfaces of the volume body to be separated are defined by the predefined pattern and the interfaces are generated by means of an interaction of the individual laser pulses with the cornea by the generation of a plurality of cavitation bubbles along the circle-like tracks.

Thus, the cavitation bubbles can be generated reduced in effort. Thus, the corresponding depth relief can in particular be evaluated depending on the determined reference point, whereby the cavitation bubbles can be generated with less effort, in particular in z-direction. Thus, a reference point of a virtual axis of symmetry or a virtual center of symmetry is in particular described. For example, a center of gravity, a centroid, a barycenter or also a center of a not “perfectly” symmetric volume body can be determined as the reference point. Furthermore, it can be realized that corresponding reference points, for example the center of gravity as the reference point, can be determined by minimization with for example asymmetric Zernike polynomials. Then, it can for example be provided that the reference point does not coincide with a point of symmetry of the volume body, in particular viewed in x-y direction, whereby the depth relief can nevertheless be reliably generated at least in z-direction.

Thus, the generated paths by means of the cavitation bubbles can be generated as a type of height isolines, wherein in particular the z-direction is to be understood by height. In other words, paths are ascertained, wherein the cavitation bubbles are preferably situated substantially at a same height (iso-height) on the respective path viewed in relation to the z-direction of the laser device. The laser device can also be referred to as laser.

In particular, a human or animal eye, in particular a cornea, can be regarded as the material. Therein, the laser can be formed as an eye surgical laser. The processing apparatus can also be referred to as treatment apparatus.

Thus, the invention in particular proposes that a reference point, for example a center of gravity, is ascertained from the corresponding x-y-z coordinates for the cut of the volume body within the cornea, which in turn corresponds to a type of center of the symmetry. This can be determined both for the posterior interface and the anterior interface, in particular separately from each other. Therein, the weightings of the z-positions are in particular uniformly distributed around this reference point. This point, which corresponds to the reference point, can then in turn represent a start point or an end point for generating the cavitation bubbles, in particular along a path or a track. In other words, this means that the beginning of the generation of the cavitation bubbles does not correspond to the center of the treatment, but that the reference point is deliberately determined in decentered manner to generate simpler movements of the laser device viewed in z-direction. This decentration can be performed by means of for example a scanner device of the processing apparatus. Alternatively or additionally, the decentration can also be performed by means of a movement of the eye or of the patient. This means that the patient or the eye itself can also be docked to the system and be shifted to the scanner device, or else the system can be deliberately and automatically dock the patient in decentered manner such that the neutral position of the scanner is situated in this barycenter. From this point of time, the virtual height isolines can be generated according to whether the reference point has been defined as start or end, wherein the virtual height isolines are thus generated with minimum z-effort by means of the cavitation bubbles in particular viewed in z-direction. This is advantageous since the scanner is in particular to be slower moved in z-direction than in x-y direction as is known.

In particular, that direction is to be understood by z-direction, which extends substantially parallel to the laser beam and/or to the optical axis of the laser device. The x-direction and the y-direction are then in turn to be regarded perpendicularly to the z-direction, wherein the x-direction is also formed perpendicularly to the y-direction.

Alternatively to the center of symmetry by means of center of gravity, it can also be reversely proceeded, and the height isolines can also be first determined and then the center of symmetry can in turn be determined for example by means of a centroid of all of the height isolines, whereby a pseudo center of all of the possible height isolines is then in turn determined. Again alternatively thereto, a spiral or circular or elliptical tracing of the cavitation bubble paths with in particular reduced z-effort can for example also be simply performed instead of the height isolines. Herein, it can occur at the edge by the decentration that a so-called clipping, thus “tailoring”, has to be performed, for example typically with a type of optical shutter or a pulse picker to achieve the desired shape with respect to the treatment center, in particular clinically and not technically considered, at the end.

Therein, an advantageous form of configuration provides that a possible tilt, i.e. a pivot, is additionally determined based on the x-y-z coordinates or the height isolines, and it can also be deliberately compensated for by a further decentration, for example depending on the curvature of a patient interface. Thus, in this case, not the scanner itself is shifted, but either the shift is effected via the patient interface or via the eye such that the curvature of the patient interface with respect to the eye counteracts this tilt.

Again alternatively, it can for example be provided that not the x-y-z coordinates of the cut itself within the cornea are used, but it is used with x-y-z coordinates of the cut from the view of the or in relation to the patient interface. It in particular has a zero position, which does not have to coincide with the cornea coordinates. In particular if a curved user interface/patient interface is for example used, the x-y-z coordinates would also view the sagitta, thus with a circular arc, the distance from the center of the arc to the center of its basis, of the user interface based on the user interface, whereby a lower effort for the scanner arises.

Again alternatively, it can be provided that neither the x-y-z coordinates of the cut, nor the x-y-z coordinates of the patient interface are used, but the x-y-z coordinates of the cut from the view of the scanner, in particular viewed in z-direction, which in particular corresponds to the corresponding control values. The scanner itself in turn has a different zero position. The x-y-z coordinates of the scanner device would not only also consider the sagitta of the patient interface, but also the different refractive indices and geometries of the optical components and thus also the different displacement paths per scanner increment such that a lower effort for the scanner arises.

The depth relief is in particular the volume body itself, thus the difference between anterior and posterior interface. Thus, the anterior and posterior interfaces are in particular determined based on the depth relief such that the lenticule corresponds to this depth relief. Further, the reference point can be determined both on the anterior and the posterior interface. Alternatively or additionally, a common reference point can also be determined for the anterior and the posterior interface.

Therein, it is in particular provided that the posterior interface is for example first generated and then the anterior interface is generated thereafter in time. Alternatively or additionally, the anterior interface and only then the posterior interface can also be generated. Again alternatively, it is possible that the cavitation bubbles are for example generated substantially at the same time both for the posterior interface and for the anterior interface. Herein, it can for example be provided that a cavitation bubble is first generated within the posterior interface and then a cavitation bubble is in turn generated as the next cavitation bubble within the anterior interface.

According to an advantageous form of configuration, the depth relief is determined at the posterior interface. Thus, the depth relief is in particular only to be generated at the posterior interface. Thus, a structure or shape or course of the depth relief is in particular determined at the posterior interface. Therein, the anterior interface can for example be generated substantially parallel to a surface of the eye. Thus, it is allowed in simple manner to generate the volume body.

It is further advantageous if the control data is generated such that the anterior interface is generated substantially parallel to a surface of the material, in particular of the eye. Thus, the generation of the anterior interface can in particular be achieved in simple manner. Furthermore, it is allowed that the volume body and in particular then the depth relief is in particular reliably generated for example at the posterior interface.

A further advantageous form of configuration provides that spiral tracks or elliptical tracks are generated as substantially circle-like tracks. Thus, it is allowed that the cavitation bubbles can in turn be generated along the spiral tracks depending on the reference point in simple manner such that the laser device or the processing apparatus can be operated with less effort.

It is also advantageous if the reference point is determined depending on the thickest location of the volume body to be generated or on the thinnest location of the volume body. Therein, the thinnest location in particular for example corresponds to a minimum depth and the thickest location to a maximum depth of the volume body. This is in particular to be understood in z-direction. Alternatively or additionally, the highest or deepest location, viewed in z-direction in relation to the volume body, of the respective interface can also be used as the respective reference point. Thus, different reference points can be used such that the method is flexibly employable.

Further, it has proven advantageous if a mathematical minimizing method for minimizing an asymmetry of the depth relief is used for determining the reference point. For example, a rotating (rotational) asymmetry can be minimized by means of the mathematical model. Furthermore, it is to be noted at this point that the asymmetry of the respective interfaces can also be minimized.

Furthermore, it can be provided that a potential position change of the eye as the material in relation to the laser and/or a potential position change of the laser in relation to the eye are taken into account in controlling the laser. Thus, minimum movements of the eye in relation to the laser or of the laser in relation to the eye can in particular also be taken into account, whereby errors in generating the cavitation bubbles can be minimized. Thus, the volume body can be generated in improved manner.

According to a further advantageous form of configuration, the reference point is determined as the beginning of the circle-like track or as the end of the circle-like track. Thus, it is possible that the reference points can be flexibly generated for the patient, whereby it can for example be responded to individual needs of the patient. Further, it can be reacted to corresponding situations during the treatment as well as the construction of the processing apparatus itself can also be taken into account therein.

Furthermore, it has proven advantageous if the reference point is determined such that it does not coincide with a center of symmetry of the volume body viewed in the direction of the cavitation bubbles to be generated. Thus, the center of symmetry of the volume body and the reference point are in particular differently formed. Thus, the reference point is determined independently of the center of symmetry of the volume body and is preferably only dependent on the depth relief to be generated.

It is further advantageous if a shape of a patient interface of the processing apparatus for docking the material, in particular the eye, in the treatment is taken into account in determining the reference point. In particular, the patient interface has a zero position, which does not have to coincide with the cornea coordinates. In particular if a curved user interface is for example used, the x-y-z coordinates would also consider the sagitta, thus with a circular arc, the distance from the center of the arc to the center of its basis, of the user interface based on the user interface, whereby a lower effort for the scanner arises.

In a further advantageous form of configuration, a lenticular volume body is removed from the corneal volume by means of photodisruption or the volume body is removed by means of an ablative method. Thus, the correction can be performed in two different manners and for example also by two differently formed processing apparatuses.

According to a further advantageous form of configuration, the control of the laser is effected such that the laser emits laser pulses in a wavelength range between 300 nanometers and 1400 nanometers, in particular between 700 nanometers and 1200 nanometers, at a respective pulse duration between 1 fs and 1 ns, in particular between 10 fs and 10 ps, and a repetition frequency of greater than 10 kHz, in particular between 100 kHz and 100 MHz. Such lasers are already used for photodisruptive methods for example in the eye surgery. The produced lenticule, which corresponds to the volume body, is subsequently removed via an incision in the cornea. The use of photodisruptive lasers in the method according to the invention additionally has the advantage that the irradiation of the cornea is not to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy is ensured in the generation of the interfaces.

It is further advantageous if the control of the laser is effected such that topographic and/or pachymetric and/or morphologic data of the cornea is taken into account. Thus, topographic and/or pachymetric measurements of the cornea to be treated as well as the type, the position and the extent of the for example pathological and/or unnaturally altered area within the stroma of the cornea as well as corresponding visual disorders of the eye can in particular be taken into account. Presently, this data in particular corresponds to the preset parameter or the patient information. In particular, control datasets are generated at least by providing topographic and/or pachymetric and/or morphologic data of the untreated cornea and providing topographic and/or pachymetric and/or morphologic data of the pathological and/or unnaturally altered area to be removed within the cornea or considering corresponding optical corrections for eliminating the visual disorders.

A second aspect of the invention relates to a processing apparatus with at least one laser for the separation of a volume body of a human or animal eye by means of photodisruption or by means of an ablative method and with at least one control device for the laser or lasers, which is formed to execute the steps of the method according to the preceding aspect. In addition, the processing apparatus includes a rotation scanner for predefined deflection of the laser beam of the laser towards the material to be treated, in particular the eye.

Therein, the laser is suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz.

The processing apparatus can also comprise a plurality, wherein plurality in particular means at least two, of control devices, which then in turn are formed to perform the method according to the invention. The control device or the control devices in particular comprise(s) electronic components like processors, circuits, for example integrated circuits, and further electronic components to be able to perform corresponding method steps.

In an advantageous form of configuration of the processing apparatus, the processing apparatus comprises a storage device for at least temporary storage of at least one control dataset, wherein the control dataset or datasets include(s) control data for positioning and/or focusing individual laser pulses in the cornea, and includes at least one beam device for beam guidance and/or beam shaping and/or beam deflection and/or beam focusing of a laser beam of the laser. Therein, the mentioned control datasets are usually generated based on a measured topography and/or pachymetry and/or morphology of the cornea to be treated and/or the type of the pathologically and/or unnaturally altered area to be removed within the cornea and/or the visual disorder of the eye to be corrected.

Further features and the advantages thereof can be taken from the descriptions of the first inventive aspect, wherein advantageous configurations of each inventive aspect are to be regarded as advantageous configurations of the respectively other inventive aspect.

A third aspect of the invention relates to a computer program including commands, which cause the processing apparatus according to the second inventive aspect to execute the method steps according to the first inventive aspect. A fourth aspect of the invention relates to a computer-readable medium, on which the computer program according to the third inventive aspect is stored. Further features and the advantages thereof can be taken from the descriptions of the first and second inventive aspects, wherein advantageous configurations of each inventive aspect are to be regarded as advantageous configurations of the respectively other inventive aspect.

BRIEF DESCRIPTION OF THE DRAWINGS

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

In the figures, identical or functionally identical elements are provided with the same reference characters.

DETAILED DESCRIPTION

Figure 1:
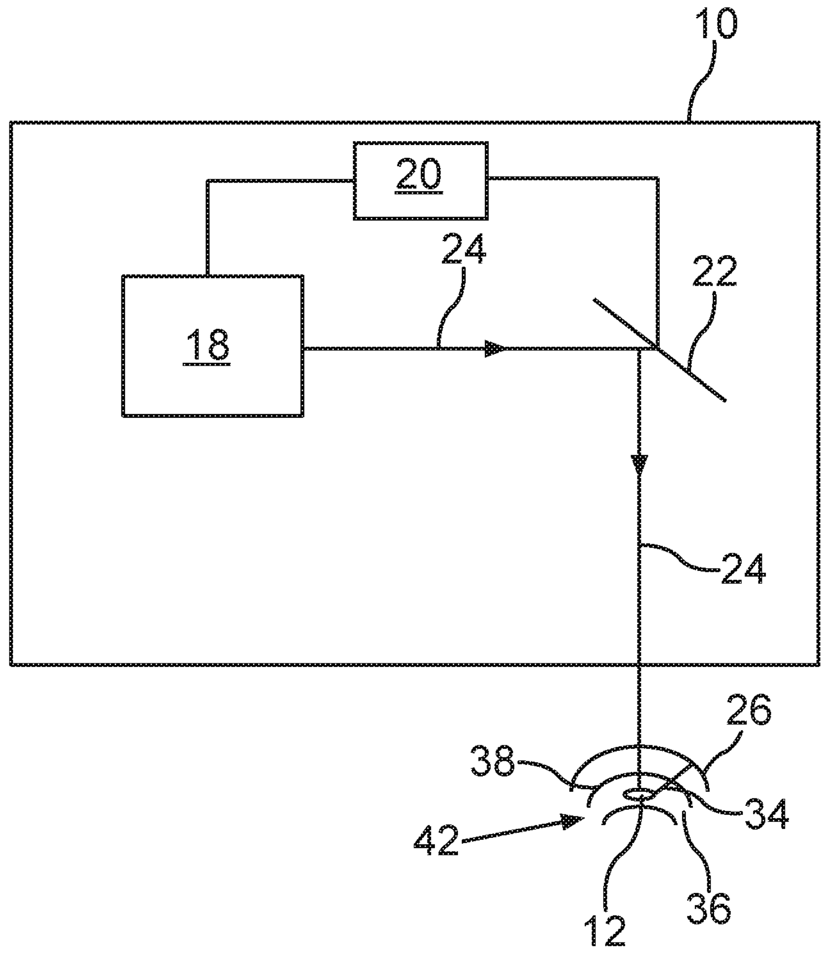
FIG. 1 is a schematic side view of an embodiment of a processing apparatus.

FIG. 1 shows a schematic representation of a processing apparatus 10 with a laser 18 for the separation of a predefined corneal volume or volume body 12. A cornea 44 (FIG. 3) comprises predefined interfaces 14, 16 (FIG. 2), wherein the cornea 44 is in particular that of a human or animal eye 42. The volume body 12 can be generated by means of photodisruption. Alternatively, the volume body 12 can also be removed by means of an ablative method. In particular, a posterior actual interface 14 and an anterior actual interface 16 of the cornea 44 are shown. One recognizes that a control device 20 for the laser 18 is formed beside the laser 18 such that it emits pulsed laser pulses for example in a predefined pattern into the cornea 44, wherein interfaces 14, 16 of the volume body 12 to be separated are generated by the predefined pattern for example by means of photodisruption. The processing apparatus 10 can also comprise further control devices. The interfaces 14, 16 of the volume body 12 form a lenticular volume body 12 in the illustrated embodiment, wherein the position of the volume body 12 is selected in this embodiment such that a pathological and/or unnaturally altered area 32 (see FIG. 2), for example a visual disorder, within a stroma 36 of the cornea 44 is enclosed. Furthermore, it is apparent from FIG. 1 that the so-called Bowman's membrane 38 is formed between the stroma 36 and an epithelium 28.

Furthermore, one recognizes that the laser beam 24 generated by the laser 18 is deflected towards a surface 26 of the cornea by means of a beam device 22, namely a beam deflection device, such as for example a rotation scanner (scanner, scanner device). The beam deflection device is also controlled by the control device 20 to generate the mentioned predefined pattern in the cornea.

The illustrated laser 18 is a photodisruptive laser or a laser 18, which is formed to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz. Alternatively, the laser 18 can also be formed for removing the volume body 12 by an ablative method.

In addition, the control device 20 comprises a storage device (not illustrated) for at least temporary storage of at least one control dataset, wherein the control dataset or datasets include(s) control data for positioning and/or for focusing individual laser pulses in the cornea 44. The position data and/or focusing data of the individual laser pulses are generated based on a previously measured topography and/or pachymetry and/or the morphology of the cornea and the pathological and/or unnaturally altered area 32 for example to be removed or the optical visual disorder correction to be generated within the stroma 36 of the eye 42. Further, data, such as for example the shape and the position, of the posterior actual interface 14 of the cornea 44 and of the anterior actual interface 16 of the cornea 44 is also determined. Below, this data is also referred to as preset parameter.

Figure 2:
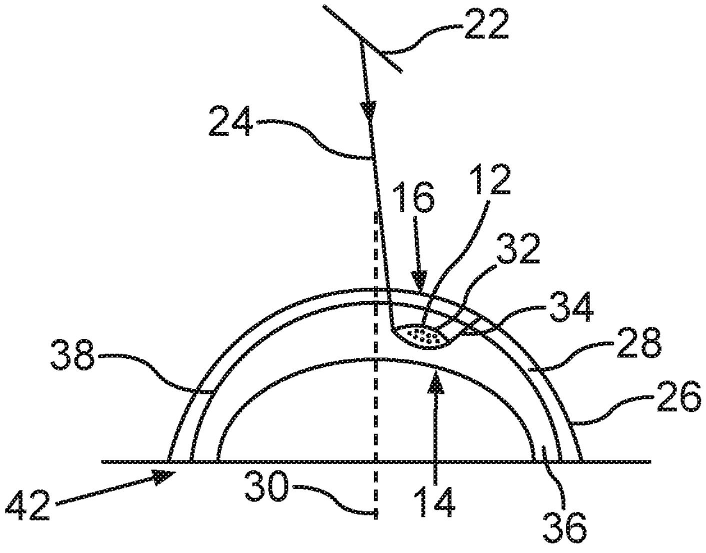
FIG. 2 is a further schematic side view of an embodiment of a processing apparatus.

FIG. 2 shows a schematic diagram of the generation of the volume body 12 to be separated according to an embodiment of the present method. One recognizes that the interfaces 14, 16 of the volume body 12 are generated by means of the pulsed laser beam 24, which is directed towards the cornea 44 or towards the surface 26 of the cornea 44 via the beam deflection device 22. Therein, the interfaces 14, 16 of the volume body 12 form a lenticular volume body 12, which for example encloses the pathological and/or unnaturally altered area 32 within the stroma 36. Furthermore, the laser 18 generates a further incision 34 in the illustrated embodiment, which intersects the volume body 12 at a predefined angle and with a predefined geometry and is formed up to the surface 26 of the cornea 44. The volume body 12 defined by the interfaces 14, 16 can then be removed from the cornea 44 via the incision 34. In the illustrated embodiment, the pathological and/or unnaturally altered area 32 is formed within the stroma 36 and outside of an optical axis 30 of the eye 42.

In the illustrated embodiment, the interface located deeper, that is the interface of the volume body 12 located deeper in the eye 42 and the stroma 36, respectively, can first be generated by means of the laser beam 24. This can be effected by at least partially circularly and/or spirally guiding the laser beam 24 according to the predefined pattern. Subsequently, the interface of the volume body 12 located higher is generated in comparable manner such that the interfaces 14, 16 form the lenticular volume body 12. Subsequently, the incision 34 is also generated by the laser

18. However, the order of the generation of the interfaces 14, 16 of the volume body 12 and of the incision 34 can also be changed.

Figure 3:
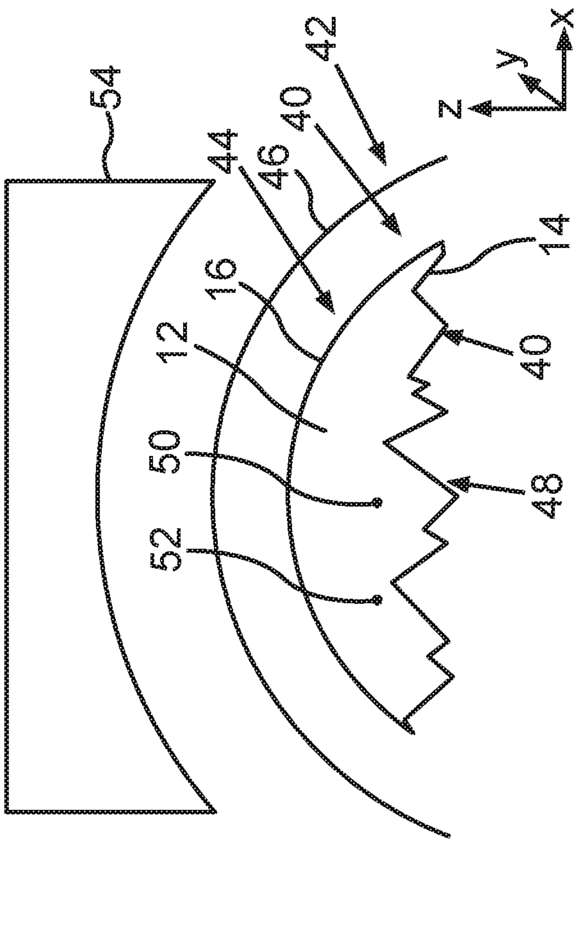
FIG. 3 is a schematic sectional view of a material, in particular of an eye.

FIG. 3 shows a schematic sectional view of the eye 42 with the volume body 12. In particular, it is shown that the volume body 12 comprises the anterior interface 16 as well as the posterior interface 14. Presently, the eye 42 in particular corresponds to a material. In the present embodiment, the anterior interface 16 is in particular formed substantially parallel to a surface 46 of the eye 42. The posterior interface 14 in turn comprises a depth relief 48. The volume body 12 comprises a center 50 of symmetry. Further, a reference point 52 is shown.

In the method for controlling the laser 18 of the processing apparatus 10, the separation of the volume body 12 is effected such that the depth relief 48 of the volume body 12 to be generated between the anterior interface 16 and the posterior interface 14 is determined depending on the at least one information, in particular patient information. The reference point 52 of an axis of symmetry of the determined depth relief 48 or of a respective interface 14, 16 is determined by means of the control device 20. Then, controlling the laser 18 starting from the determined reference point 52 in tracks circle-like at least in certain areas is in turn effected such that it emits pulsed laser pulses in a shot sequence in a predefined pattern into the cornea 44, wherein the interfaces 14, 16 of the volume body 12 are defined by the predefined pattern and the interfaces 14, 16 are generated by means of an interaction of the individual laser pulses with the cornea 44 by the generation of a plurality of cavitation bubbles 40 along the circle-like tracks. Therein, it can in particular be provided that the circle-like tracks are spiral tracks or elliptical tracks.

The point 50 of symmetry is in particular a point of symmetry, in particular viewed in x-y direction. The reference point 52 is in particular a center of symmetry with respect to the z-coordinate. In particular, as shown in FIG. 3, the reference point 52 is determined such that it does not coincide with the center 50 of symmetry of the volume body 12 viewed in the direction of the cavitation bubbles 40 to be generated.

In particular, that direction is to be understood by z-direction, which extends substantially parallel to the laser beam 24 and/or to an optical axis of the beam device 22 or laser device. The x-direction and the y-direction are then in turn to be regarded perpendicularly to the z-direction, wherein the x-direction is also formed perpendicularly to the y-direction.

Therein, it can be provided that the reference point 52 is for example determined depending on the thickest location of the volume body 12 to be generated or a thinnest location of the volume body 12. Further, it is in particular provided that a mathematical minimizing method for minimizing an asymmetry of the depth relief 48 is used for determining the reference point 52.

Furthermore, it can be provided that a potential position change of the eye 42 in relation to the laser 18 and/or a potential position change of the laser 18 in relation to the eye 42 are taken into account in controlling the laser 18.

As already mentioned, the reference point 52 can therein be considered as the beginning of the circle-like track or also as the end of the circle-like track.

Furthermore, it is shown in FIG. 3 that a shape of a patient interface 54 of the processing apparatus 10 for docking the eye 42 in the treatment is also taken into account in determining the reference point 52. In particular, a deformation of the eye 42 in docking to the patient interface 54 can be taken into account in determining the reference point 52.

Figure 4:
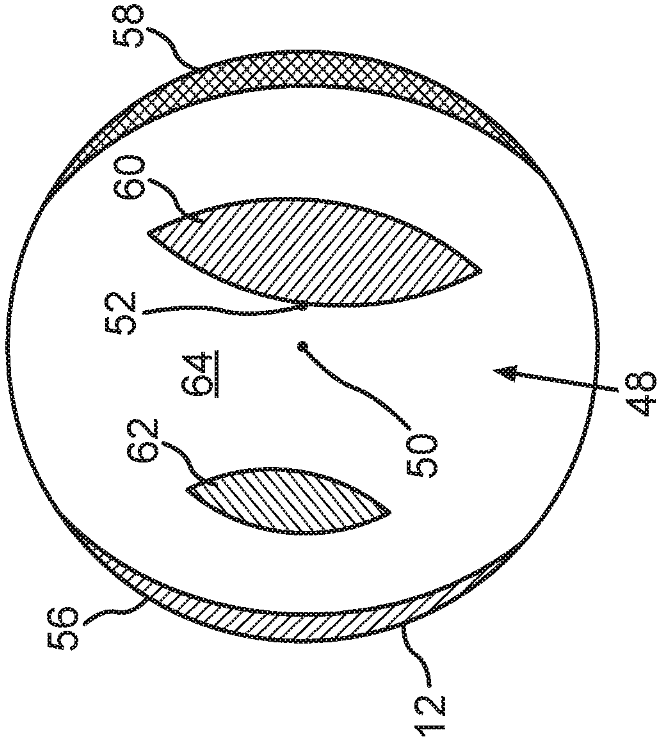
FIG. 4 is a schematic top view to an exemplary volume body.

FIG. 4 shows a top view to a volume body 12. In particular, a depth relief 48 is illustrated. For example, a first area 56 is not situated as deep in the cornea 44 as a second area 58. Furthermore, it can be provided that a third area 60 is in turn in the same depth as the first area 56. A fourth area 62 can in turn be situated deeper than the first area 56 and the second area 60, wherein the fourth area 62 is in turn situated higher than the third area 58. Further, a fifth area 64 is shown, which is in turn substantially on a same depth plane, and is for example situated higher than the areas 56, 58, 60, 62. In particular, a so-called Zernike polynomial is shown in FIG. 4.

Now, it is in particular provided that the reference point 52 is determined depending on the "altitudes" of these areas 56, 58, 60, 62 and is used as the start point or end point of the cavitation bubbles 40 to be generated, and not the center 50 of symmetry of the volume body 12 to be generated.

What is claimed is:

1. A method for controlling a laser of a processing apparatus for separation from a material of a volume body with an anterior interface and with a posterior interface, wherein the method is executed by a control device of the processing apparatus and comprises:

determining a depth relief of the volume body to be generated between the anterior interface and the posterior interface depending on at least one information;

determining a reference point of an axis of symmetry of the depth relief or of a respective anterior or posterior interface by means of the control device; and controlling the laser starting from the reference point in substantially circle-like tracks at least in certain areas such that the laser emits pulsed laser pulses in a shot sequence in a predefined pattern into the material, wherein the anterior and posterior interfaces of the volume body to be separated are defined by the predefined pattern and the anterior and posterior interfaces are generated by interaction of each of the laser pulses with the material by generation of a plurality of cavitation bubbles along the substantially circle-like tracks, wherein the reference point is determined depending on a thickest location of the volume body to be generated or a thinnest location of the volume body to be generated, wherein a mathematical minimizing method for minimizing an asymmetry of the depth relief is used for determining the reference point.

2. The method according to claim 1, wherein the depth relief is determined at the posterior interface.

3. The method according to claim 1, wherein control data is generated such that the anterior interface is generated substantially parallel to a surface of the material.

4. The method according to claim 1, wherein spiral tracks or elliptical tracks are generated as the substantially circle-like tracks.

5. The method according to claim 1, wherein control data is generated for removing the volume body in an eye and/or in a cornea of a human or an animal.

6. The method according to claim 5, wherein a potential position change of the eye in relation to the laser and/or a potential position change of the laser in relation to the eye are taken into account in controlling the laser.

7. The method according to claim 1, wherein the reference point is determined as a beginning of the substantially circle-like tracks or as an end of the substantially circle-like tracks.

8. The method according to claim 1, wherein the reference point is determined such that the reference point does not coincide with a center of symmetry of the volume body viewed in a direction of the plurality of cavitation bubbles to be generated.

9. The method according to claim 1, wherein a shape of a patient interface of the processing apparatus for docking the material in a processing operation is taken into account in determining the reference point.

10. The method according to claim 1, wherein the volume body is a lenticular volume body.

11. The method according to claim 1, wherein controlling the laser is effected such that topographic and/or pachymetric and/or morphologic data of the material is taken into account.

12. The method according to claim 1, wherein controlling the laser is effected such that the laser emits laser pulses in a wavelength range between 300 nm and 1400 nm, at a respective pulse duration between 1 fs and 1 ns, and a repetition frequency of greater than 10 kHz.

13. A processing apparatus with at least one laser for separation of a volume body with predefined interfaces from a material by means of photodisruption or ablation and with at least one control device for the at least one laser that is configured to execute the method according to claim 1.

14. The processing apparatus according to claim 13, wherein the control device comprises at least one storage device for at least temporary storage of at least one control dataset, wherein the at least one control dataset includes control data for positioning and/or for focusing individual laser pulses in the material; and includes at least one beam device for beam guidance and/or beam shaping and/or beam deflection and/or beam focusing of a laser beam of the at least one laser.

15. A non-transitory computer-readable medium, on which a computer program is stored, the computer program including commands, which cause a processing apparatus with at least one laser for separation of a volume body with predefined interfaces from a material by means of photodisruption or ablation and with at least one control device for the at least one laser to execute the method according to claim 1.

16. A method for performing a surgical procedure for separation from a material of a volume body with an anterior interface and with a posterior interface, wherein the method is executed by a control device of a processing apparatus and comprises:

determining a depth relief of the volume body to be generated between the anterior interface and the posterior interface depending on at least one information;

determining a reference point of an axis of symmetry of the depth relief or of a respective one of the anterior or posterior interface by means of the control device; and controlling a laser starting from the reference point in substantially circle-like tracks at least in certain areas such that the laser emits pulsed laser pulses in a shot sequence in a predefined pattern into the material, wherein the anterior and posterior interfaces of the volume body to be separated are defined by the predefined pattern and the anterior and posterior interfaces are generated by interaction of each of the laser pulses with the material by generation of a plurality of cavitation bubbles along the substantially circle-like tracks, wherein the reference point is determined depending on a thickest location of the volume body to be generated or a thinnest location of the volume body to be generated, wherein a mathematical minimizing method for minimizing an asymmetry of the depth relief is used for determining the reference point.

17. The method for performing a surgical procedure according to claim 16, wherein the depth relief is determined at the posterior interface.

18. The method for performing a surgical procedure according to claim 16, wherein control data is generated such that the anterior interface is generated substantially parallel to a surface of the material.

19. The method for performing a surgical procedure according to claim 16, wherein spiral tracks or elliptical tracks are generated as the substantially circle-like tracks.

20. The method for performing a surgical procedure according to claim 16, wherein control data is generated for removing the volume body in an eye and/or in a cornea of a human or an animal.

21. The method for performing a surgical procedure according to claim 20, wherein a potential position change of the eye in relation to the laser and/or a potential position change of the laser in relation to the eye are taken into account in controlling the laser.

22. The method for performing a surgical procedure according to claim 16, wherein the reference point is determined as a beginning of the substantially circle-like tracks or as an end of the substantially circle-like tracks.

23. The method for performing a surgical procedure according to claim 16, wherein the reference point is determined such that the reference point does not coincide with a center of symmetry of the volume body viewed in a direction of the plurality of cavitation bubbles to be generated.

24. The method for performing a surgical procedure according to claim 16, wherein a shape of a patient interface of the processing apparatus for docking the material in a processing operation is taken into account in determining the reference point.

25. The method for performing a surgical procedure according to claim 16, wherein the volume body is a lenticular volume body.

26. The method for performing a surgical procedure according to claim 16, wherein controlling the laser is effected such that topographic and/or pachymetric and/or morphologic data of the material is taken into account.

27. The method for performing a surgical procedure according to claim 16, wherein controlling the laser is effected such that the laser emits laser pulses in a wavelength range between 300 nm and 1400 nm, at a respective pulse duration between 1 fs and 1 nss, and a repetition frequency of greater than 10 kHzz.

28. The method according to claim 1, wherein controlling the laser is effected such that the laser emits laser pulses in a wavelength range between 700 nm and 1200 nm, at a respective pulse duration between 10 fs and 10 ps, and a repetition frequency of between 100 kHz and 10 MHz.

29. The method for performing a surgical procedure according to claim 16, wherein controlling the laser is effected such that the laser emits laser pulses in a wavelength range between 700 nm and 1200 nm, at a respective pulse duration between 10 fs and 10 ps, and a repetition frequency of between 100 kHz and 10 MHz.

* * * * *